United States Patent [19]

van Hes et al.

[11] 4,439,440
[45] Mar. 27, 1984

[54] 1-ALKOXYCARBONYLPHENYLCARBAMOYL-3-PHENYL-4-CYANOALKYL-2-PYRAZOLINES AND USE AS INSECTICIDES

[75] Inventors: Roelof van Hes; Arnoldus C. Grosscurt, both of Weesp, Netherlands

[73] Assignee: Duphar International Research B.V., Weesp, Netherlands

[21] Appl. No.: 375,869

[22] Filed: May 7, 1982

[30] Foreign Application Priority Data

May 12, 1981 [NL] Netherlands ............... 8102310

[51] Int. Cl.³ .................. A01N 43/56; C07D 231/06
[52] U.S. Cl. .................. 424/273 P; 548/379
[58] Field of Search .................. 548/379; 424/273 P Primary Examiner—Henry R. Jiles
Assistant Examiner—Kurt Briscoe
Attorney, Agent, or Firm—Stevens, Davis, Miller & Mosher

[57] ABSTRACT

The invention relates to new pyrazoline derivatives having insecticidal activity; the new compounds can be represented by the general formula

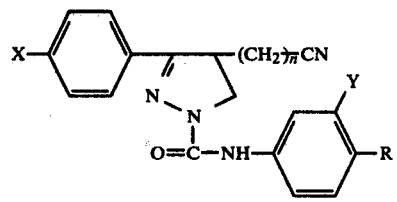

wherein
R is an alkoxycarbonyl group having 2 to 6 carbon atoms,
X and Y are equal or different and represent hydrogen atoms or halogen atoms,
and n is 2, 3 or 4.

After having been processed to compositions, the compounds may be used for the control of insects in a dosage from 0.01 to 1 kg of active substance per hectare.

7 Claims, No Drawings

1-ALKOXYCARBONYLPHENYLCARBAMOYL-3-PHENYL-4-CYANOALKYL-2-PYRAZOLINES AND USE AS INSECTICIDES

The invention relates to new pyrazoline derivatives and to a method of preparing the new compounds. The invention also relates to insecticidal compositions on the basis of the new compounds and to the use of these compositions for controlling insects.

British Patent Specification No. 1,570,635 describes substituted phenyl carbamoyl-2-pyrazolines having insecticidal activity, for example, 1-(4-chlorophenyl-carbamoyl)-3-(4-chlorophenyl)-4-(3-cyanopropyl)-2-pyrazoline.

It has now been found surprisingly that pyrazoline derivatives which, in particular as regards the substituent at the phenyl carbamoyl group differ from the known compounds, show a significantly better insecticidal activity than the above known compound.

Therefore, the present invention is characterized by new pyrazoline derivatives of the general formula

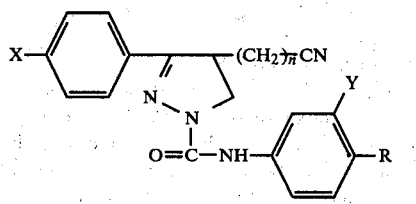

wherein

R is an alkoxy carbonyl group having 2 to 6 carbon atoms,

X and Y are equal or different and represent hydrogen atoms or halogen atoms, and n is 2, 3 or 4.

Particularly effective insecticides prove to be new compounds of the general formula

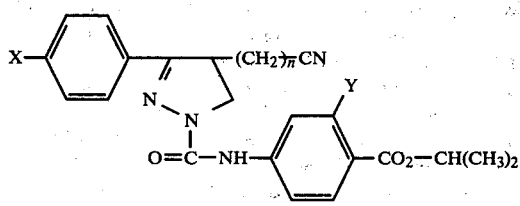

wherein X, Y and n have the above-given meanings.

Examples of particularly effective insecticides are:

(1) 1-(4-isopropoxycarbonylphenylcarbamoyl)-3-(4-chlorophenyl)-4-(3-cyanopropyl)-2-pyrazoline;
(2) 1-(4-isopropoxycarbonylphenylcarbamoyl)-3-(4-chlorophenyl)-4-(2-cyanoethyl)-2-pyrazoline;
(3) 1-(4-isopropoxycarbonylphenylcarbamoyl)-3-(4-chlorophenyl)-4-(4-cyanobutyl)-2-pyrazoline;
(4) 1-(3-chloro-4-isopropoxycarbonylphenylcarbamoyl)-3-(4-chlorophenyl)-4-(3-cyanopropyl)-2-pyrazoline; and
(5) 1-(3-chloro-4-isopropoxycarbonylphenylcarbamoyl)-3-(4-chlorophenyl)-4-(2-cyanoethyl)-2-pyrazoline.

Examples of other new pyrazoline derivatives according to the invention which have an interesting insecticidal activity are:

(6) 1-(4-ethoxycarbonylphenylcarbamoyl)-3-(4-chlorophenyl)-4-(2-cyanoethyl)-2-pyrazoline;
(7) 1-(4-sec.butoxycarbonylphenylcarbamoyl)-3-(4-chlorophenyl)-4-(2-cyanoethyl)-2-pyrazoline;
(8) 1-(4-ethoxycarbonylphenylcarbamoyl)-3-(4-chlorophenyl)-4-(3-cyanopropyl)-2-pyrazoline;
(9) 1-(4-methoxycarbonylphenylcarbamoyl)-3-(4-chlorophenyl)-4-(3-cyanopropyl)-2-pyrazoline;
(10) 1-(4-sec.butoxycarbonylphenylcarbamoyl)-3-(4-chlorophenyl)-4-(3-cyanopropyl)-2-pyrazoline;
(11) 1-(4-methoxycarbonylphenylcarbamoyl)-3-(4-chlorophenyl)-4-(4-cyanobutyl)-2-pyrazoline;
(12) 1-(3-chloro-4-isopropoxycarbonylphenylcarbamoyl)-3-(4-chlorophenyl)-4-(4-cyanobutyl)-2-pyrazoline;
(13) 1-(4-sec.butoxycarbonylphenylcarbamoyl)-3-(4-chlorophenyl)-4-(4-cyanobutyl)-2-pyrazoline;
(14) 1-(4-n-propoxycarbonylphenylcarbamoyl)-3-(4-chlorophenyl)-4-(3-cyanopropyl)-2-pyrazoline; and
(15) 1-(4-n-butoxycarbonylphenylcarbamoyl)-3-(4-chlorophenyl)-4-(3-cyanopropyl)-2-pyrazoline.

The substances according to the invention may be used for the control of insects in agriculture and horticulture, in woods and in surface waters, as well as for the protection of textile against attack by, for example, moths and carpet beetles, against insects in stores, for example, in stored cereals, and against ectoparasites on domestic animals.

The substances according to the invention can also be used for the control of insects living in the manure of hot-blooded animals, such as cows, pigs and hens. For this application, the active compounds can be administered orally to the animals, for example, mixed through the food, so that they land in the manure after some time ("through-feeding").

Because of their strong insecticidal activity the substances according to the invention are even at low dosages able to efficaciously control noxious insects, such as beetles, flies and mosquitos; it has been proved that the compounds of the invention are particularly active against the larvae of these insects.

For practical applications the substances in accordance with the invention are usually processed to compositions. In such compositions the active substance is mixed with solid carrier material or dissolved or dispersed in liquid carrier material, if desired in combination with auxiliary substances, for example, emulsifiers, wetting agents, dispersion agents and stabilizers.

Examples of compositions according to the invention are aqueous solutions and dispersions, oily dispersions, solutions in organic solvents, pastes, dusting powders, dispersible powders, miscible oils, granules, pellets, invert emulsions, aerosol compositions and fumigating candles.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying apparatus by emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marlow), organic granules (for example, dried coffee grounds, cut tobacco stems and ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example, talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution; these miscible oils are also called emulsifyable concentrates. Suitable solvents are, for example, xylene, toluene, petroleum distillates which are rich in aromates, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution an emulsifier and, if desired, one or more surface-active substances have been added. When diluting with water shortly before or during spraying, an aqueous dispersion of the active substance is then obtained.

An aerosol composition according to the invention is obtained in the usual manner by incorporating the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives," for example, polyvinylalcohol cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Pesticidal compounds known per se may also be incorporated in the compositions according to the invention. As a result of this the activity spectrum of the composition is widened and synergism may occur.

For use in such a combination composition are to be considered the following known insecticidal, acaricidal and fungicidal compounds.

Insecticides, for example:
1. organic chlorine compounds, for example 6,7,8,9,10,10-hexachloro-1,5,5a,6,9,9a-hexahydro-6,9-methano-2,4,3-benzo[e]-dioxathiepine-3-oxide;
2. carbamates, for example, 2-dimethylamino-5,6-dimethylpyrimidin-4-yl dimethyl carbamate and 2-isopropoxyphenyl methylcarbamates;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethyl phosphate;
4. O,O-di(m)ethyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-5-methylpyrimidin-4-yl-, and O-4-nitrophenyl O,O-di(m)ethyl phosphorothioate;
5. O,O-di(m)ethyl phosphorodithioates, for example, S-methylcarbamoylmethyl-, S-2-ethylthioethyl-, S-(3,4-dihydro-4-oxo-benzo[d]-1,2,3-triazin-3-ylmethyl)-, S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethylphosphorodithioate;
6. phosphonates, for example, dimethyl 2,2,2-trichloro-1-hydroxy-ethylphosphonate;
7. natural and synthetic pyrethroids;
8. amidines, for example, N'-(2-methyl-4-chlorophenyl)-N,N-dimethylformamidine;
9. microbial insecticides, such as Bacillus thuringiensis; and
10. benzoyl ureas, such as N-(2,6-difluorobenzoyl)-N'-(4-chlorophenyl)urea.

Acaricides, for example:
1. organic tin compounds, for example, tricyclohexyl tin hydroxide and di[tri-(2-methyl-2-phenylpropyl)tin]oxide;
2. organic halogen compounds, for example isopropyl 4,4'-dibromobenzilate, 2,2,2-trichloro-1,1-di(4-chlorophenyl) ethanol and 2,4,5,4'-tetrachlorodiphenyl sulphone;

and furthermore: 3-chloro-α-ethoxyimino-2,6-dimethoxybenzyl benzoate and O,O-dimethyl S-methylcarbamoyl methyl phosphorothioate.

Fungicides, for example:
1. organic tin compounds, for example, triphenyl tin hydroxide and triphenyl tin acetate;
2. alkylene bisdithiocarbamates, for example, zinc ethylenebisdithiocarbamate and manganese ethylene bisdithiocarbamate;
3. 1-acyl- or 1-carbamoyl-N-benzimidazole (-2) carbamates and 1,2-bis (3-alkoxycarbonyl-2-thiureido)benzene, and furthermore 2,4-dinitro-6-(2-octylphenyl-crotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N,N'-dimethylsulphamide, tetrachloroisophthalonitrile, 2-(4'-thiazolyl)benzimidazole, 5-butyl-2-ethylamino-6-methylpyrimidine-4-yl-dimethylsulphamate, 1-(4-chlorophenoxy)-3,3-dimethyl-1(1,2,4-triazole-1-yl)-2-butanone, α-(2-chlorophenyl)-α-(4-chlorophenyl)-5-pyrimidinemethanol, 1-(isopropylcarbamoyl)-3-(3,5-dichlorophenyl)hydantoin, N-(1,1,2,2-tetrachloroethylthio)-4-cyclohexene-1,2-carboximidine, N-trichloromethylmercapto-4-cyclohexene-1,2-dicarboximidine, N-tridecyl-2,6-dimethylmorpholine, and 5,6-dihydro-2-methyl-1,4-oxathiine-3-carboxanilide.

The dosages of the composition according to the invention desired for practical application will, of course, depend on various factors, for example, field of application, selected active substance, form of composition, nature and extent of the infection and the weather conditions.

In general it holds that favourable results are obtained with a dosage which corresponds to 0.01 to 1 kg of the active substance per hectare.

For the above-described "through-feeding," the active substance is mixed through the fodder in a quantity which is effective for insecticidal applications.

The compounds according to the invention are new substances which can be prepared in a manner which is known per se for related compounds.

For example, the new compounds can be prepared by reacting a pyrazoline of the general formule

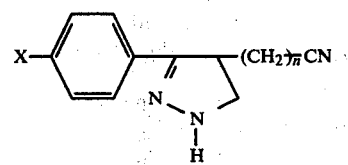

wherein X and n have the above-given meanings, with an isocyanate of the general formula

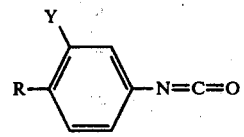

wherein R and Y have the meanings also given above. This reaction is carried out in a suitable organic solvent, for example, an ether, for example diethyl ether, an aliphatic nitrile, for example acetonitrile, a chlorinated aliphatic hydrocarbon, or an aromatic hydrocarbon, at a temperature between 0° C. and the boiling-point of the solvent used, preferably at room temperature or a slightly elevated temperature. The isocyanate to be used for this reaction can be prepared by reacting the corresponding aniline with phosgene in an inert polar organic solvent, for example an ether such as dioxane, at a reaction temperature between 0° C. and the boiling point of the solvent used.

The invention will now be described in greater detail with reference to the following specific examples.

EXAMPLE I

Preparation of 1-(4-isopropoxycarbonylphenylcarbamoyl)-3-(4-chlorophenyl)-4-(3-cyanopropyl)-2-pyrazoline.

A solution of 125.3 g of 4-isopropoxycarbonylaniline in 160 ml of dioxane was added dropwise within 30 minutes at 0°–10° C. to a solution of 100 ml of phosgene in 300 ml of dioxane while stirring. The reaction mixture was then stirred at 20° C. for 30 minutes and then heated to boiling; the solvent was distilled off and the residue was distilled under reduced pressure. The desired 4-isopropoxycarbonylphenyl isocyanate was obtained in a yield of 136.8 g; boiling point 87°–88° C./0.2 mm.

51.5 g of the above-prepared 4-isopropoxycarbonylphenyl isocyanate were added to a solution of 61.9 g of 3-(4-chlorophenyl)-4-(3-cyanopropyl)-2-pyrazoline in 450 ml of diethyl ether at room temperature. After stirring for 30 minutes at room temperature, 500 ml of petroleum ether (40–60) were added, after which the reaction mixture was stirred at room temperature for another hour. The crystalline precipitate was sucked off, washed with petroleum ether (40–60) and dried in air. 95.0 g Of 1-(4-isopropoxycarbonylphenylcarbamoyl)-3-(4-chlorophenyl)-4-(3-cyanopropyl)-2-pyrazoline were obtained. After stirring 10 g of the resulting product with 100 ml of diethyl ether, a product was obtained having a melting point of 109°–113° C.

The following compounds were prepared in a corresponding manner:

1-(4-isopropoxycarbonylphenylcarbamoyl)-3-(4-chlorophenyl)-4-(2-cyanoethyl)-2-pyrazoline, melting-point 199° C.;

1-(4-isopropoxycarbonylphenylcarbamoyl)-3-(4-chlorophenyl)-4-(4-cyanobutyl)-2-pyrazoline, melting-point 106° C.;

1-(4-ethoxycarbonylphenylcarbamoyl)-3-(4-chlorophenyl)-4-(2-cyanoethyl)-2-pyrazoline, melting-point 171° C.;

1-(4-sec.butoxycarbonylphenylcarbamoyl)-3-(4-chlorophenyl)-4-(2-cyanoethyl)-2-pyrazoline, melting-point 195° C.;

1-(4-ethoxycarbonylphenylcarbamoyl)-3-(4-chlorophenyl)-4-(3-cyanopropyl)-2-pyrazoline, melting-point 110° C.;

1-(3-chloro-4-isopropoxyphenylcarbamoyl)-3-(4-chlorophenyl)-4-(cyanopropyl)-2-pyrazoline, melting-point 140° C.;

1. -(4-sec.butoxycarbonylphenylcarbamoyl)-3-(4-chlorophenyl)-4-(3-cyanopropyl)-2-pyrazoline, melting-point 102° C.;

1-(4-methoxycarbonylphenylcarbamoyl)3-(4-chlorophenyl)-4-(4-cyanobutyl)-2-pyrazoline, melting-point 132° C.;

1-(3-chloro-4-isopropoxycarbonylphenylcarbamoyl)3-(4-chlorophenyl)-4-(4-cyanobutyl)-2-pyrazoline, melting-point 108° C.;

1-(4-sec.butoxycarbonylphenylcarbamoyl)-3-(4-chlorophenyl)-4-(4-cyanobutyl)-2-pyrazoline, melting-point 106° C.;

1-(3-chloro-4-isopropoxycarbonylphenylcarbamoyl)-3-(4-chlorophenyl)-4-(2-cyanoethyl)-2-pyrazoline, melting-point 158° C.;

1-(4-n-propoxycarbonylphenylcarbamoyl)-3-(4-chlorophenyl)-4-(3-cyanopropyl)-2-pyrazoline, melting-point 164° C.;

1-(4-n-butoxycarbonylphenylcarbamoyl)-3-(4-chlorophenyl)-4-(3-cyanopropyl)-2-pyrazoline, melting-point 182° C.; and 1-(4-methoxycarbonylphenylcarbamoyl)-3-(4-chlorophenyl)-4-(3-cyanopropyl)-2-pyrazoline, melting-point 160° C.

EXAMPLE II (a) Preparation of a solution of an active substance, namely 1-(4-isopropoxycarbonylphenylcarbamoyl)-3-(4-chlorophenyl)-4-(3-cyanopropyl)-2-pyrazoline, in a water-miscible liquid ("liquid").

20 g of the above active substance were dissolved in a mixture of 8 ml of isoforon and approximately 50 ml of dimethylformamide, after which a mixture of polyoxyethylene glycol ricinyl ether and an alkyl benzene sylphonate was added as an emulsifier in a quantity of 20 g. In a corresponding manner the other active substances were processed to 10 or 20% "liquids."

In a corresponding manner, "liquids" were obtained in N-methyl pyrrolidone, dimethylformamide, and a mixture of N-methyl pyrrolidone and isoforon as solvents.

(b) Preparation of a solution of the active substance in an organic solvent

200 Mg of the active substance to be tested were dissolved in 1,000 ml of acetone in the presence of 1.6 g of nonylphenylpolyoxyethylene. This solution was used as a spray liquid.

(c) Preparation of an emulsifiable concentrate of the active substance.

10 G of the active substance to be tested were dissolved in a mixture of 10 ml of isoforon and 70 ml of xylene; to this solution were added 10 g of a mixture of a polyoxyethylene sorbitan ester and an alkyl benzene sulphonate as an emulsifier.

(d) Preparation of a dispersible powder (W.P.) of the active substance.

25 G of the active substance to be tested were mixed with 67 g of kaolin in the presence of 1.5 g of sodiumalkylsulphate, 1.5 g of butylnaphthalene sulphonate and 5 g of lignine sulphonate.

(e) Preparation of a suspension concentrate (flowable) of the active substance.

A mixture of 5 g of the active substance, 1 g of lignine sulphonate and 0.5 g of an alkylnaphthalenesulphonate were completed with water until an overall quantity of 100 ml.

(f) Preparation of a granule of the active substance.

7.5 G of active substance, 5 g of sulphite lye and 87.5 g of ground dolomite were mixed, after which the resulting mixture was processed to a granular composition by means of the so-called compacting method.

EXAMPLE III

The growth tips of dwarf French bean plants (*Phaseolus vulgaris* L) having two well developed leaves were removed, after which the plants were sprayed until dripping with the compositions, obtained according to example II-b in different concentrations. After the plants had dried-up, they were placed in transparent plastic cylinders and then infected with 5 larvae of *Epilachna varivestis* (larvae of the Mexican bean beetle). The cylinders were then covered with lens paper and a gauze and then shelved, an alternating ligh-dark cycle of 18 hours light and 6 hours dark being used; temperature in the light 24° C., relative humidity (RH) 70%; temperature in the dark 19° C. at a RH of 80–90%. After 6 days the mortality percentage of the larvae was established. Each experiment was carried out in triplicate. The results of the tests are recorded in table A below. The numbers of the compounds in the table correspond to the numbers used in the description.

TABLE A

Insecticidal activity against larvae of *Epilachna varivestis*

| active compound | concentr. in mg of act. subst. per liter | mortality percentage |
|---|---|---|
| 1-(4-chlorophenyl-carbamoyl)-3-(4-chlorophenyl)-4-(3-cyanopropyl)-2-pyrazoline (known) | 100 | 50–90 |
| | 30 | 0–50 |
| (1) | 100 | 90–100 |
| | 30 | 90–100 |
| | 10 | 90–100 |
| | 3 | 50–90 |
| | 1 | 0–50 |
| (2) | 100 | 90–100 |
| | 30 | 90–100 |
| | 10 | 90–100 |
| | 3 | 90–100 |
| | 1 | 0–50 |
| (3) | 100 | 90–100 |
| | 30 | 90–100 |
| | 10 | 90–100 |
| | 3 | 50–90 |
| | 1 | 0–50 |
| (4) | 100 | 90–100 |
| | 30 | 90–100 |
| | 10 | 90–100 |
| | 3 | 50–90 |
| | 1 | 0–50 |
| (5) | 100 | 90–100 |
| | 30 | 90–100 |
| | 10 | 90–100 |
| | 3 | 90–100 |
| | 1 | 0–50 |
| (6) | 100 | 90–100 |
| | 30 | 50–90 |
| | 10 | 0–50 |
| (7) | 100 | 90–100 |
| | 30 | 50–90 |
| | 10 | 0–50 |
| (8) | 100 | 90–100 |
| | 30 | 90–100 |
| | 10 | 0–50 |
| (9) | 100 | 90–100 |
| | 30 | 0–50 |
| | 10 | 0–50 |
| (10) | 100 | 90–100 |
| | 30 | 50–90 |
| | 10 | 0–50 |
| (11) | 100 | 90–100 |
| | 30 | 90–100 |
| | 10 | 0–50 |
| (12) | 100 | 90–100 |
| | 30 | 90–100 |
| | 10 | 90–100 |
| | 3 | 0–50 |
| (13) | 100 | 90–100 |

TABLE A-continued

| active compound | concentr. in mg of act. subst. per liter | mortality percentage |
|---|---|---|
|  | 30 | 90–100 |
|  | 10 | 90–100 |
|  | 3 | 0–50 |
| (14) | 100 | 90–100 |
|  | 30 | 90–100 |
|  | 10 | 90–100 |
|  | 3 | 90–100 |
|  | 1 | 0–50 |
| (15) | 100 | 90–100 |
|  | 30 | 50–90 |
|  | 10 | 50–90 |
|  | 3 | 0–50 |

EXAMPLE IV

20 Larvae of *Aedes aegypti* (larvae of the yellow fever mosquito) were brought in aqueous suspensions of the active substances in various concentrations obtained according to example II. These suspensions are maintained at a temperature of 25° C. for 10 days, during which incubation period the larvae are fed with an aqueous suspension of powdered brown bread and yeast. The mortality percentage is determined after 10 days taking into account the natural mortality. The results of the experiments are recorded in table B. The numbers of the compounds in the table correspond to the numbers used in the description. The meanings of the symbols stated in the table are as follows:

+ = 90–100% mortality
± = 50–90% mortality
− = <50% mortality

TABLE B

Insecticidal activity against larvae of *Aedes aegypti*.

| active compound | activity; concentration in mg of act. subst. p l. |  |  |  |  |
|---|---|---|---|---|---|
|  | 1 | 0.3 | 0.1 | 0.03 | 0.01 |
| (1) | + | + | ± | − |  |
| (2) | + | ± | ± | ± | − |
| (4) | + | + | − |  |  |
| (6) | + | + | − |  |  |
| (8) | + | − |  |  |  |
| (10) | + | − | − |  |  |
| (11) | + | + | − |  |  |
| (12) | + | + | + | − |  |
| (15) | + | ± | ± | ± | − |

EXAMPLE V

Young plants of Brussels sprouts (*Brassica deracea*), approximately 15 cm high, are sprayed with composition of active substances in various concentrations obtained according to example II. After the plants have dried up they are placed in transparent plastic cylinders and then infected with 5 larvae of *Pieris brassicae* (caterpillars of the cabbage white butterfly). The cylinders are then covered with a gauze and stored, in alternating light-dark cycle of 18 hours light and 6 hours dark being used; temperature in the light 24° C., relative humidity (RH) 70%; temperature in the dark 19° C. at a RH of 80–90%. After 5 days the mortality percentage of the larvae is established. Each experiment is carried out three-fold. The results of the experiments are stated in table C below. The number of the compounds in the table correspond to the numbers used in the description.

TABLE C

Insecticidal activity against larvae of *Pieris brassicae*

| active compound | concentr. in mg of act. subst. per liter | mortality percentage |
|---|---|---|
| (1) | 100 | 90–100 |
|  | 30 | 90–100 |
|  | 10 | 90–100 |
|  | 3 | 90–100 |
|  | 1 | 90–100 |
|  | 0.3 | 0–50 |
| (2) | 100 | 90–100 |
|  | 30 | 90–100 |
|  | 10 | 90–100 |
|  | 3 | 90–100 |
|  | 1 | 50–90 |
|  | 0.3 | 0–50 |
| (3) | 100 | 90–100 |
|  | 30 | 90–100 |
|  | 10 | 90–100 |
|  | 3 | 50–90 |
|  | 1 | 50–90 |
|  | 0.3 | 0–50 |

We claim:

1. A pyrazoline of the formula

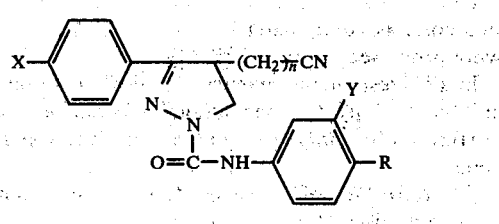

wherein
R is an alkoxycarbonyl group having 2 to 6 carbon atoms,
X and Y are equal or different and represent hydrogen atoms or halogen atoms, and
n is 2, 3 or 4.

2. A pyrazoline of the formula

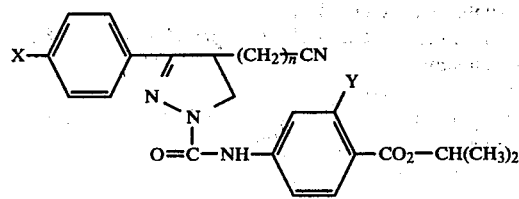

wherein, X, Y and n have the meanings given in claim 1.

3. 1-(4-Isopropoxycarbonylphenylcarbamoyl)-3-(4-chlorophenyl)-4-(3-cyanopropyl)-2-pyrazoline.

4. An insecticidal composition, characterized in that, in addition to a solid or liquid inert carrier material, the composition comprises an insecticidally effective amount of a compound of the general formula

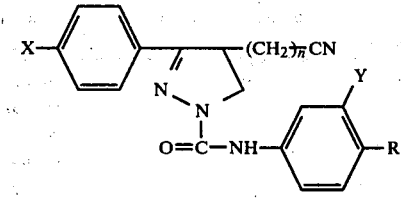

wherein R, X, Y and n have the meanings given in claim 1,

5. A composition as claimed in claim 4, characterized in that the active constituent is a compound of the general formula

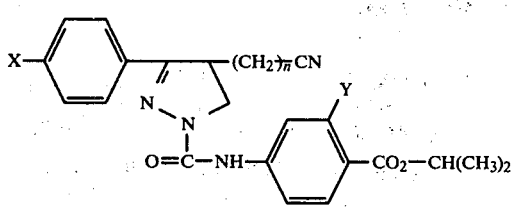

wherein X, Y and n have the meanings given in claim 1.

6. A composition as claimed in claim 4, characterized in that the active constituent is 1-(4-isopropoxycarbonylphenylcarbamoyl)-3-(4-chlorophenyl)-4-(3-cyanopropyl)-2-pyrazoline.

7. A method of controlling insects, characterized in that the infested area is treated with a composition as claimed in any one of claims 4–6 in a dosage from 0.01 to 1 kg of active substance per hectare.

* * * * *